United States Patent
Alexander (12) 
(10) Patent No.: US 6,230,347 B1
(45) Date of Patent: May 15, 2001

(54) ORTHOPEDIC COMFORT PILLOW

(76) Inventor: Christina Alexander, Suite 2005, 65 Harbour Square, Toronto (CA), M5J2L4

( * ) Notice: Subject to any disclaimer, the term of this patent is extended or adjusted under 35 U.S.C. 154(b) by 0 days.

(21) Appl. No.: 09/171,249
(22) PCT Filed: Apr. 15, 1997
(86) PCT No.: PCT/CA97/00244
§ 371 Date: Oct. 15, 1998
§ 102(e) Date: Oct. 15, 1998
(87) PCT Pub. No.: WO97/38612
PCT Pub. Date: Oct. 23, 1997
(51) Int. Cl.[7] .................................................. A47C 20/02
(52) U.S. Cl. .................................. 5/636; 5/645; 5/655.3; 5/644
(58) Field of Search ............................ 5/636, 645, 655.9, 5/953, 640, 644, 630, 653, 655.3, 950, 951, 952

(56) References Cited

U.S. PATENT DOCUMENTS

| | | | |
|---|---|---|---|
| 3,161,436 | * 12/1964 | Hood | 5/655.9 X |
| 4,393,530 | * 7/1983 | Stark | 5/640 |
| 4,803,743 | * 2/1989 | Greenawalt | 5/636 |
| 5,016,303 | * 5/1991 | Tanaka et al. | 5/636 |
| 5,533,218 | * 7/1996 | Fahy | 5/636 |
| 5,682,633 | * 11/1997 | Davis | 5/636 |

FOREIGN PATENT DOCUMENTS

| | | |
|---|---|---|
| 1654223 | * 11/1971 | (DE) . |
| 19535940 | * 4/1996 | (DE) . |
| 2182152 | * 12/1973 | (FR) . |
| 2282964 | * 4/1995 | (GB) . |
| 9107122 | * 5/1991 | (WO) . |

\* cited by examiner

Primary Examiner—Terry Lee Melius
Assistant Examiner—James M Hewitt
(74) Attorney, Agent, or Firm—Sim, McBurney, Sim, Hughes, Ashton & McKay

(57) ABSTRACT

The use of particulate stuffings such as down or fiberfill in the construction of orthopaedic pillows has previously been limited due to formidable intrinsic difficulties: On a curved wedge of support, with natural turning movement of the sleeper, fiberfill will tend to "avalanche" downhill, settle and pack down to obliterate any initial toricity or inflected curvature. Hence the sleeper is awakened to refluff or to punch the missing inflection back into place. Though simple internal partitioning can initially delay the scenario, in due course nuisance fiber sequestering and impeded normal hand refluffing are the results. The present invention focuses on structurally overcoming these impediments to the orthopaedic use of particulate fillings. It notably provides a pillow that manifests to the sleeper as downy soft, and comfortingly restful. Yet, internally built-in are the specific elements and mechanisms for 'stealth support': A forward-reaching fiberfill overlay is carefully partitioned and co-proportioned in loft and fibre density with its underlying supporting core, to provide the inflected toric gradient of support for the sleeper. The calibrated loft of the overlay, in combination with the use of minimal stable core thickness, extensive differential slotting and feathering of the core surface, in addition to lateral fiber 'muffs', all work in tandem for the necessary dissimulation of the core, its interfaces, and the very presence of summated orthopaedic support itself. Within the overlay, angled split partitions vaulting a retrusion chamber, force the necessary support inflection into reliable existence. Furthermore, the uniquely substructured split partitions combine stretch and non-stretch fabric portions so that, with natural turning of the sleeper, they descend and recoil to lift and recirculate fibre spheres within pillow chambers. In effect, the pillow unit refluffs 'automatically', as you sleep, to refresh plumpness for undisturbed sleep throughout the night. In manufacture, the supporting core is inflatable to accommodate lower back sufferers, and further serves in Traveler Edition and Sleeping Bag applications.

32 Claims, 6 Drawing Sheets

ORTHOPEDIC COMFORT PILLOW

BACKGROUND OF THE INVENTION

The present invention relates to pillows.

Traditional pillows are essentially envelopes that are filled with a fiber stuffing and attempt to provide a uniform density throughout the pillow. In use, the stuffing fibers tend to become either compressed or displaced towards the periphery of the pillow as a result of the head and neck turning during sleep. Consequently, the head and neck would have the least amount of support where it is most needed, with the result that there is a tendency for the neck to curve in the opposite direction to normal. Such traditional pillows, therefore, are recognized as failing to support the neck properly and can disturb the natural curve and inclination of the cervical spine. This in turn can lead to cervical sprain and chronically tense, stiff and painful muscles of the upper back and neck.

An alternative structure is offered by a contoured foam pillow, in which foam blocks are shaped into thick blunt-ended bolsters. These bolsters behave as an unyielding static bulk even if turned upside down. Chiropractic literature has indicated that such bolsters thrust the cervical spine outward from its normal spinal alignment and inadequately allow for retrusion of the head. Furthermore, the foam structures that are formed on the surface of the bolster tend to splay open on the naturally convex surface of the mattress. This tends to result in a kink in the cervical spine with attendant muscle cramps and spasms, and a backward tilt of the head with attendant facial endema and respiratory consequences.

The blunt-ended bolsters typically have a concave surface and a planar surface with compliant formations projecting upwardly from the surface. These formations are intended to accommodate the curvature of the head while also providing an overall foam support.

A further prior proposal has utilized a case with a quilted wall into which can be placed static foam block supports of different thicknesses and configurations. This arrangement, however, simply provides a compliant covering for the foam blocks which therefore suffer from the same disadvantages as the contoured foam pillow.

DE 195 35 940 discloses a pillow of complex shape that tapers towards a forward edge.

None of the devices known to the applicant attempt to provide an inflected curved wedge of support for the neck.

It is therefore an object of an aspect of the present invention to provide a pillow that obviates or mitigates the above disadvantages.

SUMMARY OF THE INVENTION

In general terms, the present invention provides a pillow having a compliant base. Such compliant base is generally referred to herein as a foam base, which is preferred, but other compliant bases e.g. inflated bases may be used. In preferred embodiments, the foam base has oppositely-directed concave surfaces. A compliant overlay is provided on one of the surfaces, such that the foam base in combination with the overlay provide an inflected curved wedge of support. In particular, the overlay is divided into a plurality of chambers filled with compliant materials that provide, in combination with the foam base, an inflected density gradient or firmness gradient from front to rear of the upper surface.

Preferably the concave undersurface provides a convex pivot point which facilitates elevation of a leading edge of the foam base upon application of a load.

Accordingly, an aspect of the present invention provides a pillow comprising a compliant base extending from a front edge to a rear edge, said base having a compliant overlay thereon of lighter density than said base, said base and compliant overlay cooperatively forming a curved wedge of support from said front edge towards said rear edge, the compliant overlay extending forward of said front edge.

In another aspect, the present invention provides a pillow comprising a compliant base extending from a front edge to a rear edge, said base having opposed concave surfaces transverse to said front and rear edges, said base having a compliant overlay thereon of lighter density than said base with the compliant overlay extending forward of said front edge, said base in combination with said compliant overlay increasing in firmness of support between said front edge and said rear edge.

In preferred embodiments of the pillow, the compliant base is a foam base.

In further embodiments, the wedge or gradient is inflected.

In a further embodiment, the compliant overlay has a plurality of chambers extending transversely, said chambers being filled with compliant material of differing densities such that density of the overlay, in combination with the compliant base, in general increases from the front edge to the back edge.

Another aspect provides a pillow comprising a compliant base extending from a front edge to a rear edge, said base having a compliant overlay attached thereon of lighter density than said base, said base and compliant overlay cooperatively forming a curved wedge of support from said front edge towards said rear edge.

BRIEF DESCRIPTION OF THE DRAWINGS

The present invention is illustrated by the embodiments shown in the drawings, in which:

FIG. 12 is a schematic representation of a view on the line A—A of FIG. 1, and shows a location for the valve of FIG. 10. In another embodiment 92 of FIG. 13, particularly for use in a sleeping bag 93, the foam base may be replaced with an inflatable bladder such as 90 of FIG. 10, with the overlay 14 being located thereon, and having a valve 91 such as shown by general example in FIGS. 10, 11, and 12.

DETAILED DESCRIPTION OF THE PREFERRED EMBODIMENTS

Figure 1:
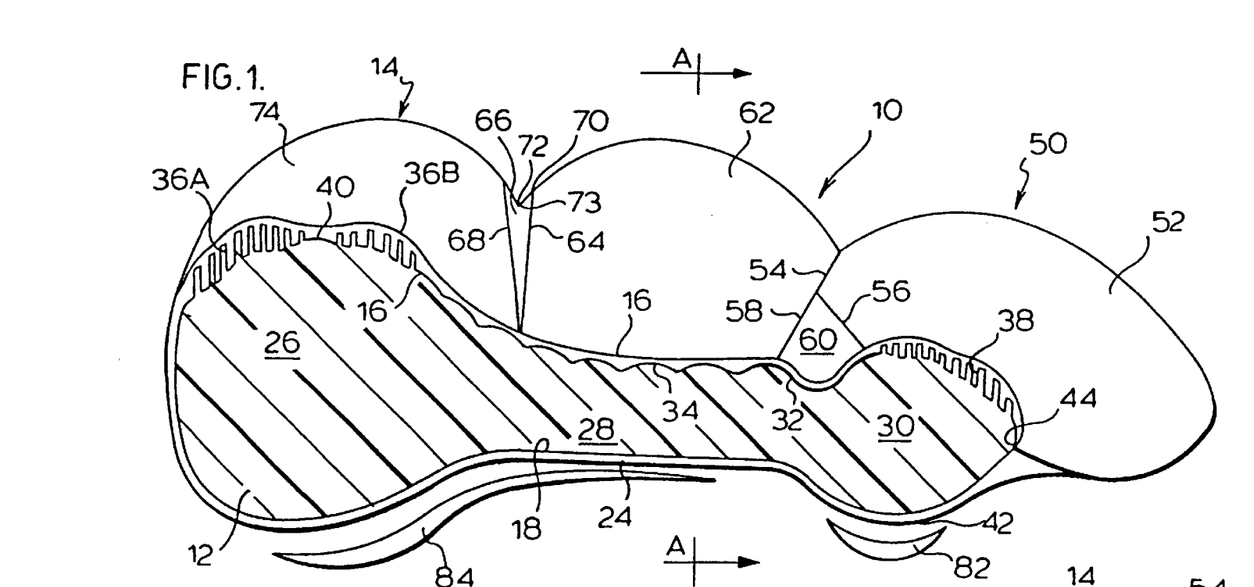
FIG. 1 is a schematic representation of a side view in section of a pillow.
Figure 2:
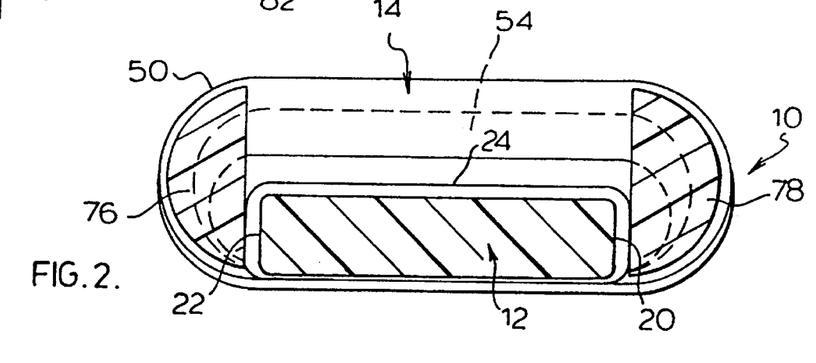
FIG. 2 is a schematic representation of a view on the line A—A of FIG. 1.

Referring therefore to the drawings and in particular to FIGS. 1 and 2, a pillow generally indicated at 10 has a core or base 12 and overlay 14. Base 12 is formed from a flexible cellular foam, examples of which are synthetic or natural latex foam or low density polyurethane foam, typically having a density in the order of 1.1 to 1.2 lb./ft.$^3$ (17.6–19.2 kg/m$^3$), and has oppositely directed concave faces 16 and 18. Concave face 16 is upwardly directed to support overlay 14, whereas concave face 18 is intended for engagement with a support surface e.g. preferably the upper surface of a spring coil mattress with peripheral convex curvature or crowning.

In the preferred embodiment shown in FIGS. 1 and 2, base 12 is of uniform cross-section and extends laterally between planar end faces 20 and 22 as shown in FIG. 2. Base 12 is enclosed within fabric case 24 which generally conforms to the outer surface of base 12. Case 24 is formed from a lightweight fabric, typically a polycotton such as a matt lustre chintz or broadcloth with a thread count greater than 180 cut on the grain. However, it will be appreciated that a wide variety of fabrics may be used to enclose base 12.

The concave upper and lower surfaces 16,18 define three distinct areas within base 12, namely back bolster 26, waisted midsection 28, and bulbous front section 30. Bulbous front section 30 and waisted midsection 28 are separated by trough 32 formed in the upper surface 16 of base 12.

Upper surface 16 is formed with scalloped ridges indicated by 34, which in back bolster 26 and front section 30 are surmounted with upstanding parallel fingers 36, 38, respectively that project upwardly from the scallops 34. In the embodiment shown, which is a preferred embodiment, the outer (upper) edges of fingers 36A,36B define a trough 40 in upper surface 16; it is understood, however, that fingers 36A and 36B may be omitted with trough 40 being formed in surface 16. Such fingers tend to break up the interface of the foamed core, to reduce awareness to the sleeping person. This may be viewed as dividing the interface of the foam core, in combination with surface scalloping e.g. transverse scalloping with an orthogonal intercalated cut gradient, into individual "mini-pillows" to tend to eliminate awareness of the foam interface.

Increased depth and frequency of the intercalated cuts in the center of midsection 28 results in a softer, lower loft of support to cradle the head during back sleeping. Decreasing depth and frequency of intercalated cuts towards the periphery results in a firmer higher loft of support to accommodate side-sleeping, namely to compensate for shoulder width and thus help maintain smooth spinal alignment side sleeping by reducing sideways head-drop and therefore cervical spinal "kink".

The lower surface 18 is generally planar in the midsection and merges smoothly with a convex pivotal surface indicated at 42 defining the lower surface of front section 30. Surface 42 intersects upper surface 16 at the leading apex of base 12.

Base 12 is configured so as to have sufficient thickness to be self-supporting but at the same time avoids excess bulk which would adversely affect the comfort of pillow 10.

Overlay 14 is formed as a set of individual chambers located within an outer covering 50. Outer covering 50 may be made of a similar material to case 24, and has a thread count sufficient to contain the fill material.

Leading chamber 52 is defined over upper surface 16 of front section 30 by a pair of partitions 54, 56 that extend between case 24 and overlay 50. Partition 54 is preferably formed from a stretch material such as an elastic, light-stretch, high thread count, two-way stretch fabric or alternatively a one-way stretch fabric with the direction of stretch inclined to upper surface 16. Partition 54 is attached to partition 56 along a line parallel to upper surface 16 of base 12. Partition 56 is preferably of a non-stretch fabric with a high thread count.

A further partition, 58, is secured between the junction of partitions 54 and 56 and extends to case 24 at a location spaced from the intersection of partition 56 with case 24. Partitions 56 and 58 therefore define a retrusion chamber 60 which bridges trough 32 formed in upper surface 16. Partition 58 is also preferably formed from a non-stretch high thread count fabric.

Partitions 54, 58 define one wall of an intermediate chamber 62 with the opposite wall being defined by partition 64 that extends from case 24 to covering 50. Partition 64 also forms one wall of a cusped chamber 66 with the opposite wall being defined by partition 68. Partitions 64 and 68 are each secured at a common location to case 24 and are each made from a durable, light stretch, high thread count, preferably two-way stretch fabric. Partition 64 is attached doubly to covering 50 as indicated at 70 and 72 by way of a foldover and restitch process to itself, at 73, that generates cusped chamber 66. In particular, partition 64 is attached to covering 50 so as to preferably form a pleat. Alternatively, partition 68 is attached in such a manner.

Partition 68 also forms the front wall of a rear chamber 74 which is formed between the converging of case 24 and covering 50. As can be seen in FIG. 2, the chambers project beyond the planar end walls 20 and 22 and wrap around the edges of the foam base 12 but do not extend across the lower surface 18.

The chambers 52,60,62,66 and 74 operate in cooperation with one another and with the foam base 12 to provide suitable support gradients and sleeping profile.

Leading chamber 52 extends forwardly from apex 44 of front section 30 and is filled with a fibre tuft type of stuffing such as DuPont Comforel® for maximum loft per unit weight of stuffing and to provide longevity between the need to refluff the contents. The protrusion of chamber 52 in front of apex 44 provides a very low density introduction to the pillow, as a result of absence of the foam base, to provide a generally progressive, but inflected, and compliant support for the neck and upper back. Opposite lateral ends of chamber 52 are filled with a pad of Holo-fil® or thermal bonded material, as indicated at 76,78 in FIG. 2. Pads 76 and 78 minimize awareness of the planar end walls 20 and 22 and provide a compliant outer surface.

Intermediate chamber 62 is preferably filled with an intermediate density soft mobile siliconized fiber, such as a blown mix of 30% Comforel™, 70% Holo-fil® or, alternatively, 100% Comforel preferably at a higher density. Chamber 62 is proportioned in loft and fiber density to co-operate with the upper surface 16 of the base to form a gently rising inflected curved wedge of support. Pads 76 and 78 are incorporated as described above.

Rear chamber 74 is filled with a firmer density layered type of stuffing, for example thermal bonded Holo-fil, to stabilize the fibres from sliding and to complete the gradually curving wedge of support. The fill of rear chamber 74 also contributes to the weight-bearing ability of back bolster 26 while imparting a soft tactile quality. Chamber 74 cushions and therefore minimizes awareness of the interface of back bolster 26. Pads 76 and 78 can again be incorporated or, alternatively, the bonded Holo-fil stuffing may be wrapped over the end walls 20 and 22.

Chambers 60,66 are not filled i.e. such chambers are empty. Retrusion chamber 60 is provided to permit a uniform interface between leading chamber 52 and intermediate chamber 62 and, because it is empty, itself creates a support inflection in the gradual rising wedge of the support generated by the overlay 14 and the base 12. This inflection or support release permits passive retrusion of the head so that the muscles, which would otherwise subconsciously begin to contract during deep sleep and attempt to push the posterior of the head into the pillow to restore natural postural retrusion, are permitted to simply rest and achieve fullest relaxation and recuperation. The support inflection provided by retrusion chamber 60 permits the use of adequately high densities of fill in leading chamber 52 and intermediate chamber 62 to reduce the frequency necessary for refluffing.

Stretched partition 54 is utilized to maintain walls 56 and 58 in their upright taut condition when pressure is relieved, as, for example, when the head is lifted or rolls during sleep. The recovery of partition 54 and the resultant tensioning of partitions 56 and 58 generates a refluffing action within leading chamber 52 to maintain compliance of overlay 14.

The cusped chamber is also left unfilled for enhanced ease of refluffing because this chamber's cusped overlay is able to unfold as an accordion pleat when stressed. The construction of the cusped chamber between partitions 72 and 70 also imparts considerable fluidity and give to the completed pillow unit, thus furthering both its comfort and longevity.

In an example of a pillow, having a width between end walls 20 and 22 of 20 inches (36.8 cm), the upper surface of chamber 52 has a length of 14.5 inches measured from apex 44 to the intersection of partition 54. The combined length of the partitions 54 and 56 is in the order of 3.5 inches (8.9 cm) and the chamber 52 is filled with 110 gm of Comforel and the pads 76 and 78 are each 25 gm. Upper surface of chamber 62 has an arcuate length of approximately 8.75 inches and the height of partition 64 is in the order of 2.5 inches (6.3 cm). Stuffing of chamber 60 is accomplished with 65 gm of Comforel and 55 gm of Holo-fil with the pads 76 and 78 each comprising 25 gm of Holo-fil. Rear chamber 74 has an upper length of approximately 9.5 inches (24.1 cm) and has a stuffing of 125 gm of thermal bonded Holo-fil and two pads 76 and 78 each comprising 25 gm of Holo-fil.

However, it is understood that these densities may be adjusted to suit particular requirements e.g. fabric "give", or preferences, although a progressive but inflected density gradient resulting in the progressive wedge configuration is to be preferred.

Figure 3A:
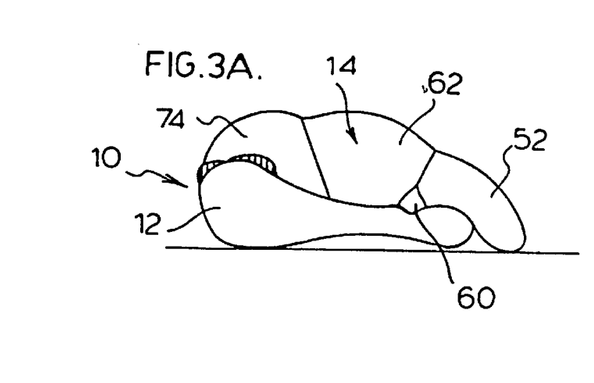
FIGS. 3a and 3b are schematic representations of a side view showing the effect of placing a load W upon the pillow shown in FIG. 1, FIG. 3a showing the pillow in an unloaded condition and FIG. 3b showing the pillow with the load W applied.
Figure 3B:
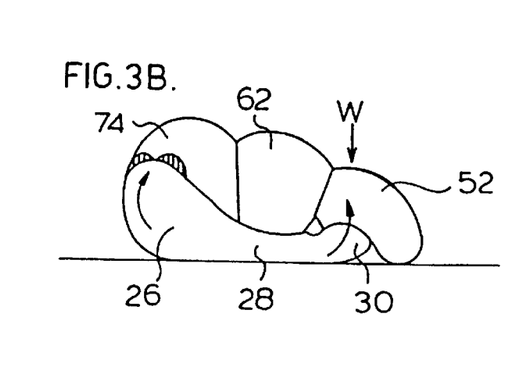

The interaction of the chambers and the base can thus be seen from FIGS. 3a and 3b in conjunction with the description above. In the free body state shown in FIG. 3a, the concave undersurface 18 is supported clear from the mattress, indicated at m, with chamber 42 projecting forwardly from foam base 12. As a load is applied to the pillow by placement of the head, concave surface 18 is flattened and a rolling occurs around pivotal surface 42. This rolling is facilitated by provision of the trough 32 so that an upward projection of apex 44 is obtained. This projection provides a mechanical lift to help gently raise and support the neck, and which is assisted by the loft and the support offered by bulbous portion 30 and retrusion chamber 60. The progressive but inflected gradient provided by the three chambers 52, 62 and 74 also assists in the muscle relaxation.

Figure 4:
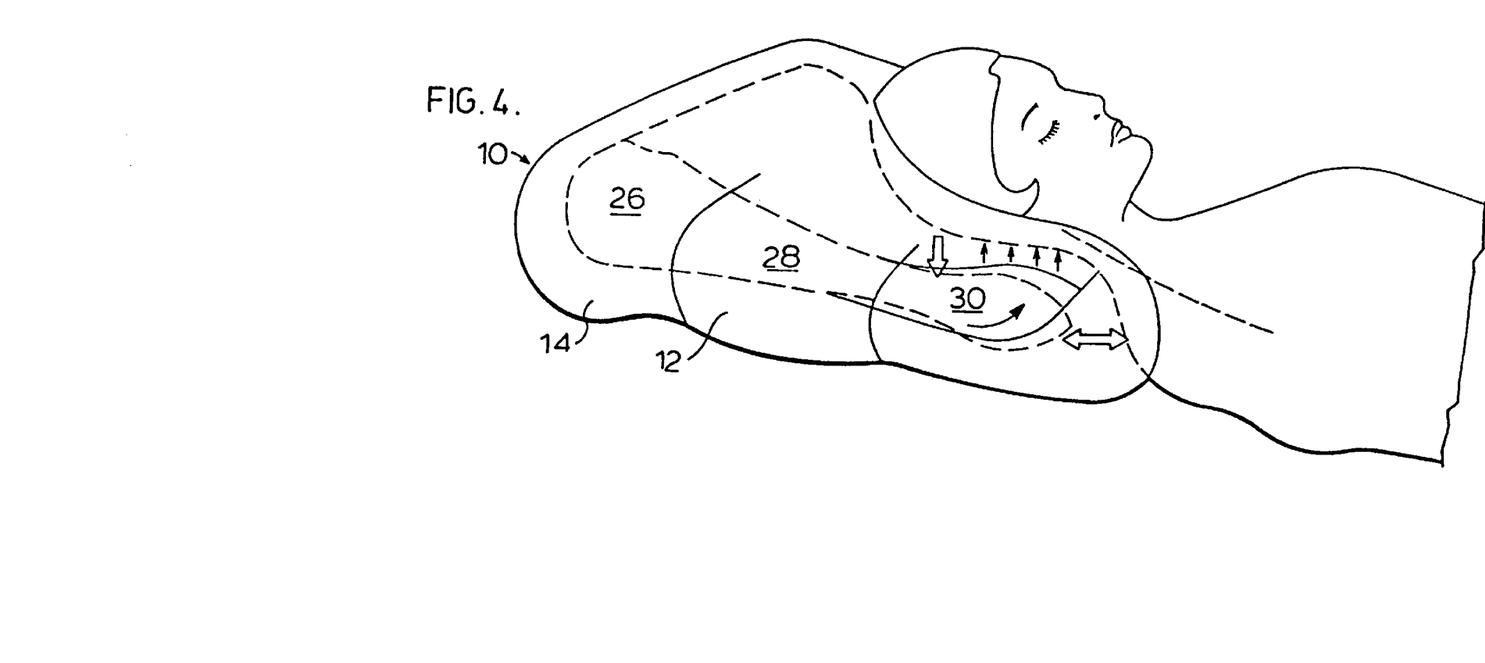
FIG. 4 is a schematic representation of a perspective view showing the pillow of FIG. 1 in use.

As can be seen from FIG. 4, as the distance between apex 44 and the user's shoulders is varied, the effective packing density provided at the leading edge of chamber 52 is varied, as is the support provided by the upper surface of bulbous front portion 30. For example, with the distance at a maximum, the lightest density of support for the lower neck and upper back is provided. If, on the other hand, the distance is minimal with the person's shoulders being adjacent apex 44, the resultant increased effective density (firmness) and support add to the support provided by base 12 and thus impart a firmer effective support to the upper back and neck. Hence, depending upon the sleeper's placement on the pillow 10, a gradual inclination or rise of approximately 4° to 7° is provided. Accordingly, a smooth spinal alignment which approaches a sleeper's natural comfortable walking posture may thus be achieved, while allowing postural muscles to rest. In this manner, the pillow promotes a restful and comfortable sleep and promotes tissue drainage for sinus and respiratory benefits.

Fingers 36 and 38 are provided to produce a gradient of vertical support at the surface of base 12, and thus reduce the awareness of base 12. Clearly, alternative surface formations or means could be used to produce a similar effect. Scallops 34 on surface 16 are provided to reduce the tendency of the fibres to slide along the base within the compartments. A similar effect may be obtained with a layer of bonded fibre although scalloping is believed to be more economical. The vertical support gradient may also be modified by forming interlaced slots in the mid section of base 12 at the upper surface 16 to reduce further the awareness of base 12.

Figure 5A:
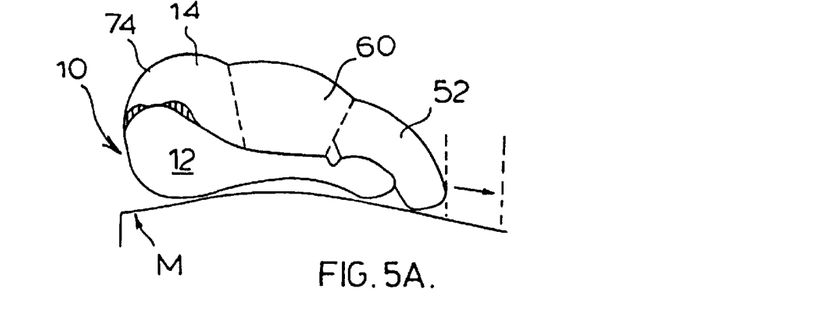
FIG. 5 is a schematic representation of a side view similar to FIGS. 3a and 3b showing the manner in which the pillow of FIG. 1 accommodates convex surfaces adjacent the edge of a mattress.
Figure 5B:
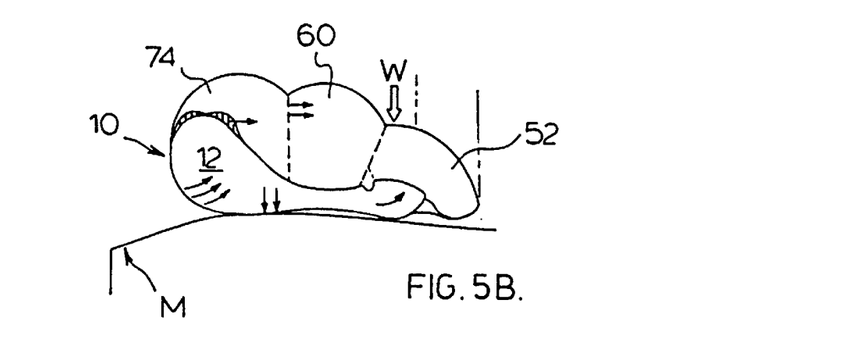

Concave undersurface 18 also co-operates with the convex surface typically found at the periphery of a mattress and is effective to increase the lofts upon application of a load to the pillow. As can be seen in FIG. 5a, the location of the pillow at the periphery of the mattress allows concave undersurface 18 to accommodate the convex surface of the mattress and provide the normal support for the user. However, with a slight forward shift of the pillow as shown in FIG. 5b, and the weight thus applied more towards the rear of the pillow, the undersurface 18 flattens, causing the rear portion of base 12 to rotate and move forwardly. This compresses intermediate chamber 62 and produces an increased loft, retrusion and effective density. Thus the smooth spinal inclination of 4° to 7° that is present in normal use can increase up to approximately 7° to 10° by the forward shift, depending on the amount of forward shift and crowning.

Figure 6:
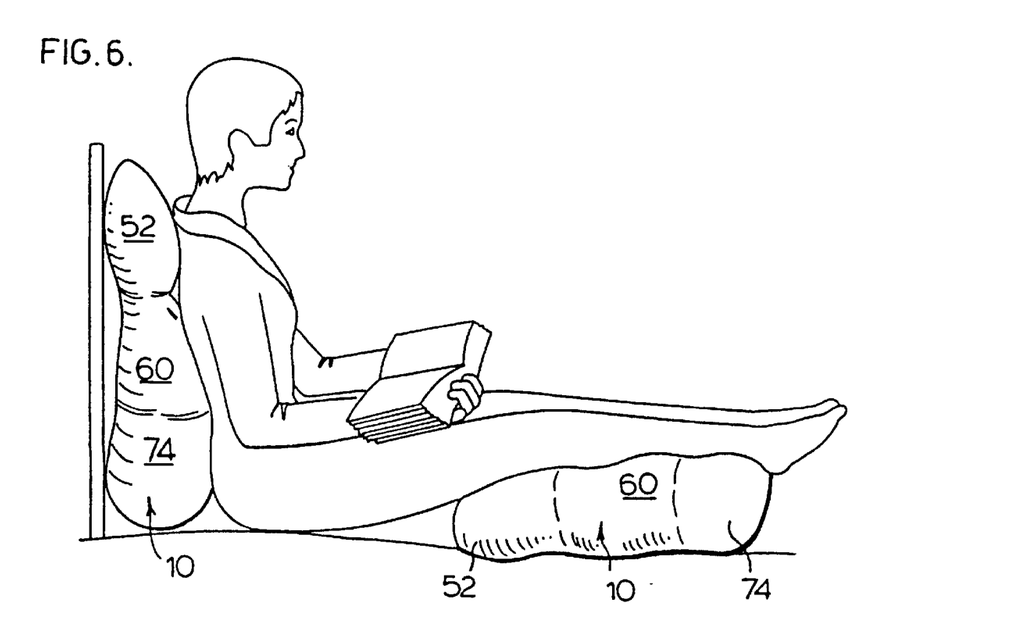
FIG. 6 is a schematic representation of a side view showing the pillow of FIG. 1 used in alternate orientations.

As may be seen in FIG. 6, pillow 10 may also be used in alternative orientations to provide support for a back and/or the legs; when used as a backrest, as shown in FIG. 6, the wedged profile accommodates the natural inclination of the back and the intermediate chamber 62 provides the lumbar support and upper sacral cushioning. However, the relatively high density of rear chamber 74 and rear portion 26 of base 12 provides a firm support for the lumbar support.

When used as a leg support, the curved wedge is conducive to allowing a gentle bend of the knees at rest, thus helping to obviate, for example, painful stretching of the posterior capsule of swollen knee joints. Retrusion chamber 60 assists with this knee bend by providing the support inflection which accommodates calf muscles and further obviates undesirable tension on the capsule of the knee joint. Elevation of the knees also reduces arching of the spine for enhanced comfort and reduced back strain.

Figures 7, 8:
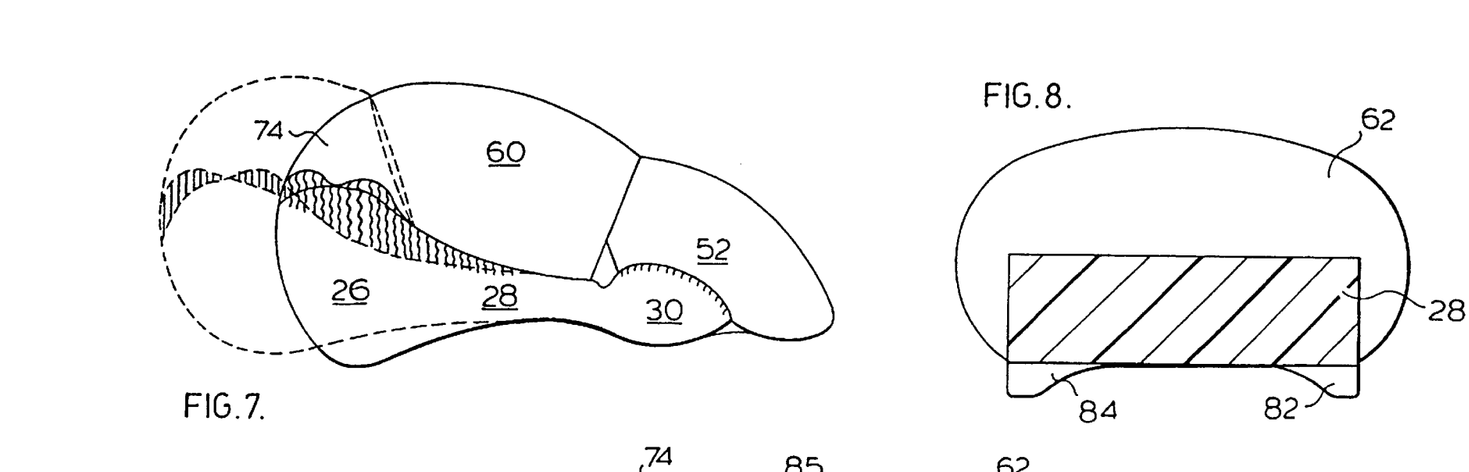
FIG. 7 is schematic representation of a side view similar to FIG. 1 showing an alternative embodiment of pillow.
FIG. 8 is a schematic representation of a transverse cross-section of an alternate embodiment of the pillow.

An alternative embodiment is shown in FIG. 7 in which pillow 10 is foreshortened so as to fit into conventional North American pillow cases e.g. 20 inch (50 cm) pillow cases. With this arrangement, a steeper wedge angle for base 12 is provided, and further surface formation at 36 reduces the awareness of the foam base and maintains the compliance of the overlay. Rear chamber 74 may be eliminated entirely in this embodiment, with the density gradient being provided by a revised contour of the surface 76.

It will be seen, therefore, that a pillow providing optimum support in a variety of uses is provided.

In the above description, base 12 has been described as of uniform cross-section but it may be sculpted in three dimensions to provide additional contours. Base 12 may be extruded or may be machined through a numerically controlled machining apparatus in which case the desired toricity can be incorporated to increase support and stability e.g. for use as a chair cushion. In the latter, laser cut drill tunnels or the like may be added for flow of air e.g. to provide a degree of cooling on movement by the user. Alternatively, base 12 could be formed from layers of different density foam, some of which could be slow recovery foams or their equivalents to increase comfort by molding to the contours of the user.

FIG. 8 shows a transverse cross-section of an embodiment of the pillow. Waisted midsection 28 has intermediate chamber 62 thereon. However in this embodiment, waisted midsection 28 has toroidal shaped sections 82 and 84 extending from the underside thereof. Toroidal shaped sections 82 and 84 are on opposed sides of the underside of waisted midsection 28. Toroidal shaped sections 82 and 84 may be part of waisted midsection 28, all being cut from the same piece of foamed material or, alternatively, cut from separate samples of material and adhered to waisted midsection 28. Preferably, toroidal shaped sections are of higher density e.g. 1.6 to 1.8 lb/cu.ft, (25.6–28.8 kg/m$^3$), compared to the density of waisted midsection 28.

Toroidal shaped sections 82 and 84 permit improved spinal alignment in backsleeping by assisting in providing a low, soft central zone in the pillow, backsleeping typically occurring in the midportion of a pillow. For sidesleeping, which typically occurs with the sleeping person situated off-center on the pillow i.e. more towards the periphery of the pillow, back toricity of the foam core of midsection 28 helps compensate for shoulder width, thereby permitting smoother alignment of the spine by helping to prevent cervical spinal "kink" attendant to sideways head drop of the sleeping person.

Figure 9:
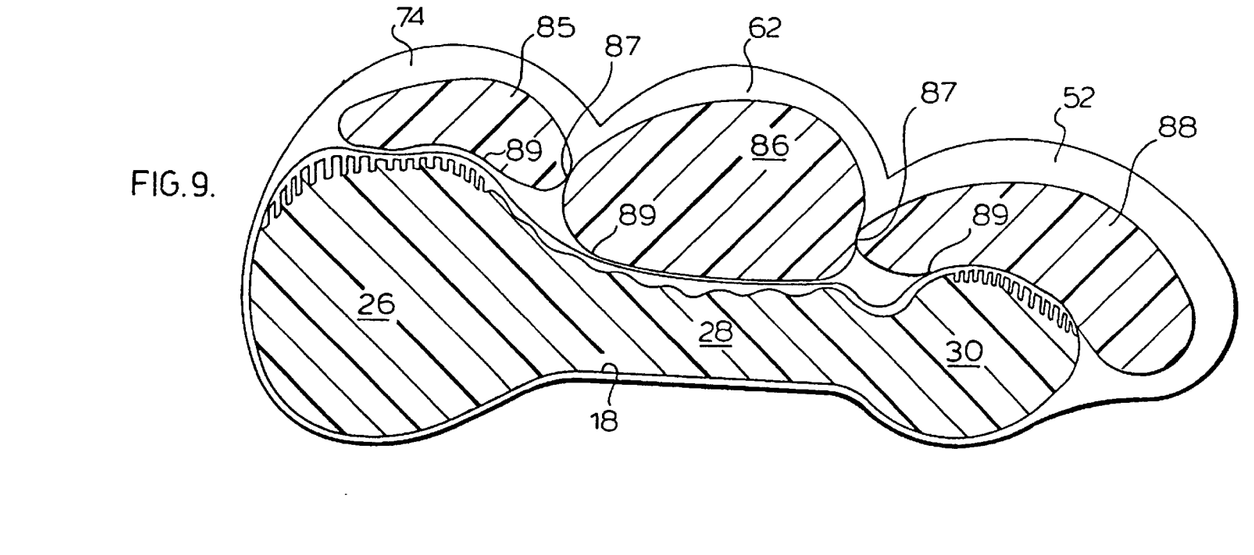
FIG. 9 is a schematic representation of a side view of an alternate embodiment of the pillow.

FIG. 9 illustrates a less preferred embodiment in which stuffed, stretchy cylindrical sock-like inserts 85, 86 and 88 can be used to replace chambers 52, 62, and 74 described previously. Each of the inserts 84, 86 and 88 is stitched or otherwise attached to the adjacent insert e.g. at 87, and attached to the foam base e.g. with glue, at 89, and preferably to the overlay 50 (not shown).

In another embodiment, particularly for use in a sleeping bag, the foam base may be replaced with an inflatable bladder, with the overlay being located thereon.

Figure 10:
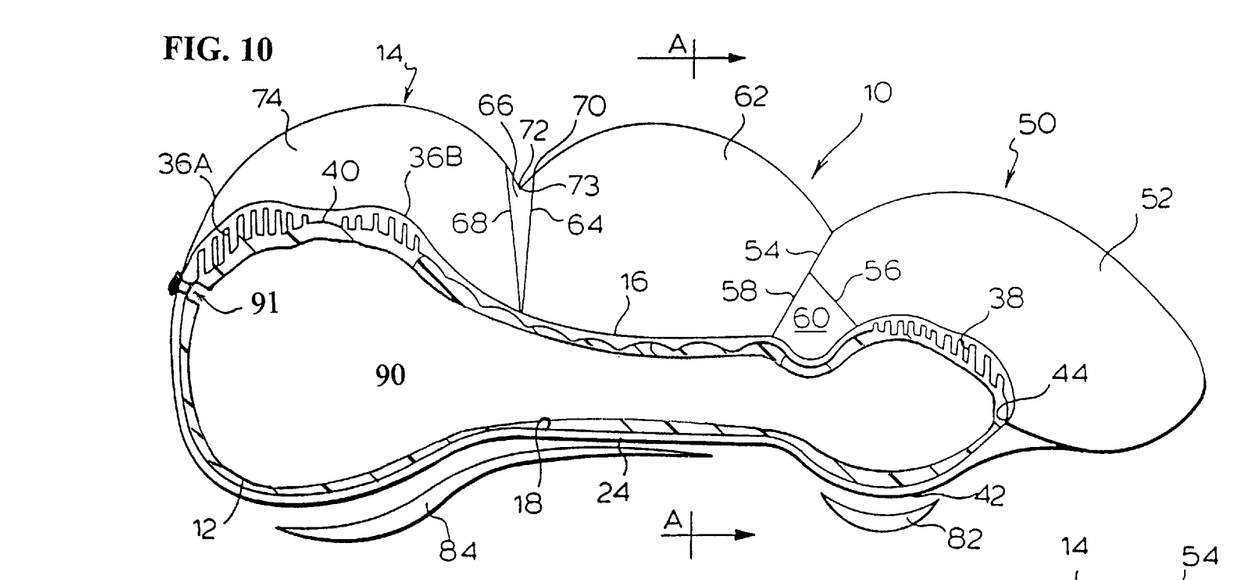
FIG. 10 is a schematic representation of a cross-sectional side view of another embodiment of the present invention showing a pillow with an inflatable supporting core and a valve.
Figure 11:
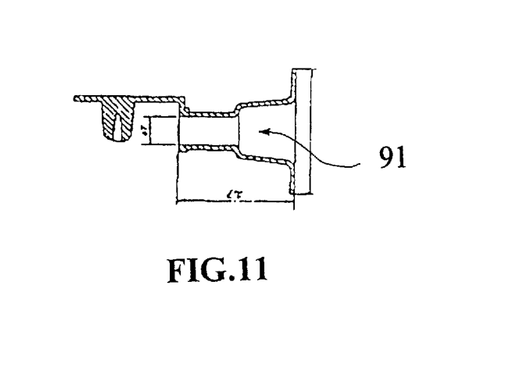
FIG. 11 is an enlarged view of the valve of FIG. 10.
Figure 12:
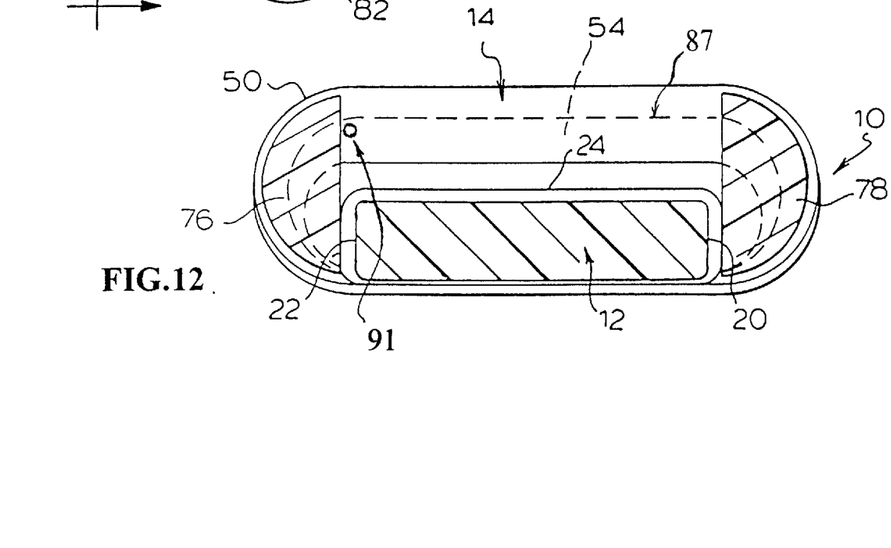
Figure 13:
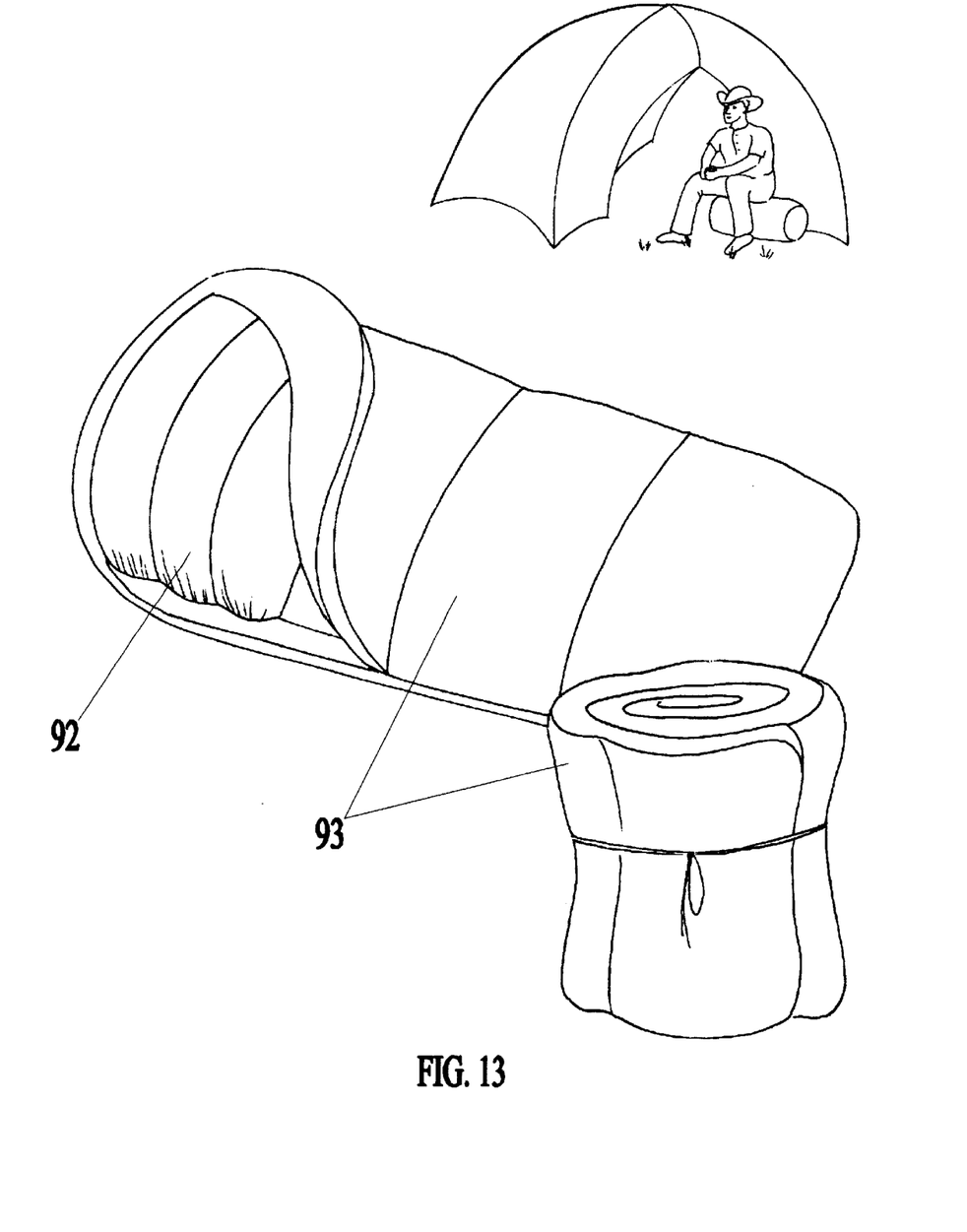
FIG. 13 is a contextual composition featuring an embodiment of the present invention 92 incorporated into a sleeping bag structure 93.

FIG. 10 represents a crossectional side view of an embodiment of the invention featuring an example of an inflatable supporting core 85, with an evacuation valve 86;

FIG. 11 is an enlarged more detailed view of an example of valve 86 of FIG. 10; and FIG. 12 shows schematically a view on the line A—A of FIG. 1, and displays by example a relative position where the valve 86 of FIG. 10 may be situated in that embodiment.

In other embodiments, additional partitions may be provided and/or angled stitching may be provided especially of the type used on some duvet quilted products.

The present invention provides a pillow, and especially a comfort pillow, that is believed to provide orthopedic benefits, that can provide improved comfort during sleeping. The pillow is of particular interest to persons who are susceptible to cervical sprains, neck and back discomforts and pains, and related discomforts.

What is claimed is:

1. A supporting device for the head and neck in sleeping, the spine in sitting, and lower body limbs in convalescence, and characterized by:

superiorly, a compliant overlay having a bounding exterior surface;

a firmer supporting core, beneath said compliant overlay, of sufficient thickness to be stable yet of dissimulative presence;

said supporting core exhibiting a front edge, a distinct midsection with top and bottom surfaces progressing into a rear edge;

said supporting core having opposed concave surfaces transverse to said front and rear edges, and a bulbous front section, a waisted mid-section and a back bolster;

said compliant overlay being formed of a plurality of chambers extending parallel to the front and rear edges, said chambers separated at least in part by means for partitioning;

said compliant overlay and said supporting core being proportioned in loft and density one relative to the other to cooperatively form a light and fluffy, unobtrusive curved wedge of support from said front edge towards said rear edge.

2. The supporting device of claim 1 in which the curved wedge of support is an inflected curved wedge of support.

3. The supporting device of claim 1 in which the chambers are filled with compliant particulate material of differing densities, the device increasing in firmness of support from the front edge to the rear edge.

4. The supporting device of claim 1 in which said means for partitioning form at least one retrusion chamber between said parallel chambers.

5. The supporting device of claim 1 in which a retrusion chamber if formed between an anterior chamber and an adjacent chamber posterior thereto, bordered below by said supporting core, said retrusion chamber extending towards the surface of the overlay.

6. The supporting device of claim 5 in which the retrusion chamber is triangular in cross-section.

7. The supporting device of claim 1 in which a retrusion chamber is formed forward of a posterior chamber, the retrusion chamber being an inverted triangle in cross-section.

8. The supporting device of claim 7 in which an apex of the inverted triangle is juxtaposed to said supporting core.

9. The supporting device of claim 4, in which said at least one retrusion chambers is an empty chamber.

10. The supporting device of claim 9 in which the said at least one retrusion chamber facilitates refluffing of said compliant overlay.

11. The supporting device of claim 5 in which the retrusion chamber provides an inflecton in said curved wedge of support.

12. The supporting device of claim 1 in which the supporting core has a tapered anterior construction.

13. The supporting device of claim 1 in which the bulbous front section and the waisted mid-section are separated by a trough formed in the top surface of said supporting core.

14. The supporting device of claim 1 in which an undercurve of the supporting core provides a gentle pivotal mechanism of lift and support when weight is applied.

15. The supporting device of claim 1 in which the supporting core provides toricity in transverse support.

16. The supporting device of claim 15 in which surface cuts assist in such toricity.

17. The supporting device of claim 1 in which the supporting core is a foam core.

18. The supporting device of claim 1 in which the supporting core is an inflatable core.

19. The supporting device of claim 1 in which the supporting core is inflatable.

20. The supporting device of claim 19 wherein the device is incorporated into a sleeping bag.

21. A supporting device for the head and neck in sleeping, the spine in sitting, and lower body limbs in convalescence, and characterized by:
   superiorly, a compliant overlay having a bounding exterior surface;
   firmer supporting core, recessed beneath said compliant overlay, of sufficient thickness to be stable yet of dissimulative presence;
   said supporting core exhibiting a front edge, a distinct midsection with top and bottom surfaces progressing into a rear edge to form a tapered anterior construction;
   said supporting core having opposed concave surfaces transverse to said front and rear edges, and a bulbous front section, a waisted midsection and a back bolster;
   said compliant overlay being formed of a plurality of chambers extending parallel to the front and rear edges, said chambers separated at least in part by means for partitioning;
   said compliant overlay and said supporting core being proportioned in loft and density one relative to the other to cooperatively form a light and fluffy, unobtrusive curved wedge of support from said front edge toward said rear edge, wherein said curved wedge of support increases in firmness from said front edge to said rear edge.

22. The supporting device of claim 21 in which the increase in firmness of support is an inflected increase in support.

23. The supporting device of claim 21 in which the increase in firmness of support is an increase in density.

24. The supporting device of claim 23 in which said chambers being filled with compliant material of differing densities such that density of the device increases from said front edge to said rear edge.

25. The supporting device of claim 21 in which the supporting core juxtaposed to said compliant overlay has a scalloped surface.

26. The supporting device of claim 21 in which the bulbous front section and the waisted mid-section are separated by a trough formed in the top surface of said core.

27. The supporting device of claim 26 in which there is a retrusion chamber between an anterior chamber and an adjacent chamber.

28. The supporting device of claim 27 in which a trough is located in the top surface of the supporting core between the bulbous front section and the waisted mid-section.

29. The supporting device of claim 27 in which a partition is formed between the anterior chamber and the adjacent chamber, said partition being at least in part formed from stretch material.

30. The supporting device of claim 29 in which the supporting core is made of foam.

31. The supporting device of claim 21, in which said overlay is attached to said supporting core.

32. The supporting device of claim 29, where the partition bifurcates to vault said trough to cooperatively form said retrusion chamber.

* * * * *